United States Patent [19]
Olson et al.

[11] Patent Number: 5,254,770
[45] Date of Patent: Oct. 19, 1993

[54] ISOMERIZATION OF AROMATIC COMPOUNDS OVER ZSM-22 ZEOLITE

[75] Inventors: David H. Olson, Pennington, N.J.; Ernest W. Valyocsik, Yardley, Pa.; R. Bruce Calvert, Plainsboro, N.J.

[73] Assignee: Mobil Oil Corp., Fairfax, Va.

[21] Appl. No.: 652,164

[22] Filed: Sep. 19, 1984

Related U.S. Application Data

[63] Continuation of Ser. No. 531,585, Sep. 13, 1983, abandoned, which is a continuation of Ser. No. 413,958, Sep. 1, 1982, abandoned.

[51] Int. Cl.$^5$ .............................................. C07C 5/27
[52] U.S. Cl. .................................................. 585/481
[58] Field of Search .................. 585/481, 480; 502/71, 502/77

[56] References Cited

U.S. PATENT DOCUMENTS

| | | | |
|---|---|---|---|
| 4,139,600 | 2/1979 | Rollmann et al. | 502/62 |
| 4,146,584 | 3/1979 | Rollmann | 585/407 |
| 4,224,141 | 9/1980 | Morrisson et al. | 585/481 |
| 4,229,282 | 10/1980 | Peters et al. | 208/111 |
| 4,344,868 | 8/1982 | Chang et al. | 252/455 Z |
| 4,351,979 | 9/1982 | Chester et al. | 585/481 |
| 4,358,397 | 11/1982 | Chu | 502/77 |
| 4,481,177 | 11/1984 | Valyocsik | 423/329 |
| 4,556,477 | 12/1985 | Dwyer | 208/11 |
| 4,574,043 | 3/1986 | Chester et al. | 208/111 |
| 4,605,488 | 8/1986 | Chester et al. | 208/11 |
| 4,717,465 | 1/1988 | Chen et al. | 208/59 |
| 4,783,555 | 11/1988 | Atkins | 502/77 |
| 4,810,357 | 3/1989 | Chester et al. | 208/97 |
| 4,814,543 | 3/1989 | Chen et al. | 585/739 |
| 4,902,406 | 2/1990 | Valyocsik | 208/118 |
| 4,919,788 | 4/1990 | Chen et al. | 208/49 |
| 5,063,038 | 11/1991 | Kirker et al. | 502/77 |
| 5,135,638 | 8/1992 | Miller | 585/739 |
| 5,137,194 | 10/1992 | Rahmim et al. | 585/671 |

*Primary Examiner*—Asok Pal
*Attorney, Agent, or Firm*—Alexander J. McKillop; Dennis P. Santini; Edward F. Kenehan, Jr.

[57] ABSTRACT

A mixture of aromatic hydrocarbons, comprising xylenes, is isomerized in the presence of ZSM-22 zeolite to produce a product stream wherein the proportion of para-xylene is substantially equal to the equilibrium ratio of the para-isomer. The process is conducted at about 500° F. to about 1100° F., at about 0 to about 3000 psig, optionally in the presence of hydrogen, and also optionally with the catalyst comprising about 0.005% to about 5.0% of a metal, e.g., platinum, palladium or cobalt, based on total catalyst weight.

15 Claims, No Drawings

ISOMERIZATION OF AROMATIC COMPOUNDS OVER ZSM-22 ZEOLITE

This application is a continuation of U.S. application Ser. No. 531,585, filed Sep. 13, 1983, now abandoned, which is a division of U.S. application Ser. No. 413,958, filed Sep. 1, 1982, now abandoned.

BACKGROUND OF THE INVENTION

1. Field of the Invention

This invention is concerned with the manufacture of aromatic compounds having six to eight carbon atoms, namely benzene, toluene and xylenes (BTX). More particularly, the invention is directed to a high temperature isomerization process conducted in the presence of the ZSM-22 zeolite.

2. Description of the Prior Art

P-xylene is a valuable chemical feedstock which may be separated for use in synthesis of polyesters from mixed xylenes by fractional crystallization. Benzene is a highly valuable product for use as a chemical raw material. Toluene is also a valuable petrochemical used as a solvent, in chemical manufacturing processes and as a high octane gasoline component.

Typically, p-xylene is derived from mixtures of $C_8$ aromatics separated from such raw materials as petroleum naphthas, particularly reformates, usually by selective solvent extraction. The $C_8$ aromatics in such mixtures and their properties are:

|  | Freezing Point °F. | Boiling Point °F. | Density Lbs./ U.S. Gallon |
|---|---|---|---|
| Ethylbenzene | −139.0 | 277.0 | 7.26 |
| P-xylene | 55.9 | 281.0 | 7.21 |
| M-xylene | −54.2 | 282.4 | 7.23 |
| O-xylene | −13.3 | 292.0 | 7.37 |

Calculated thermodynamic equilibria for the $C_8$ aromatics at 850° F. are:

| | |
|---|---|
| Wt. % ethyl benzene | 8.5 |
| Wt. % para xylene | 22.0 |
| Wt. % meta xylene | 48.0 |
| Wt. % ortho xylene | 21.5 |
| TOTAL | 100.0 |

Principal sources of such raw materials are catalytically reformed naphthas and pyrolysis distillates. The $C_8$ aromatic fractions from these sources may vary quite widely in composition, but they usually comprise about 10 to about 32 wt. % ethylbenzene, with the balance, xylenes, being divided approximately as 50 wt. % of the meta, and 25 wt. %, each of the para and ortho isomers.

Individual isomer products may be separated from the naturally occurring mixtures by appropriate physical methods. Ethylbenzene may be separated by fractional distillation, although this is a costly operation. Ortho-xylene may be separated by fractional distillation, and it is so produced commercially. Para-xylene is separated from the mixed isomers by fractional crystallization or by selective adsorption (e.g., the Parex process).

As commercial use of para and ortho xylene has increased, isomerization of the other $C_8$ aromatics to produce an equilibrium mixture of xylenes, and thus increase the yields of the desired xylenes, became increasingly important. Octafining is one of the processes which produce an increased amount of xylenes.

In a typical plant utilizing the Octafining process, a mixture of $C_8$ aromatics is introduced to an ethylbenzene tower wherein the stream is stripped of a portion of its ethylbenzene content, to an extent consistent with retaining all the xylenes in the feed stream without unduly expensive "superfractionation". Ethylbenzene is taken off as overhead, while a bottom stream, consisting principally of xylenes, together with a significant amount of ethylbenzene, passes to a xylene splitter column. The bottoms stream from the xylene splitter, comprising primarily ortho-xylene (o-xylene) and $C_9$ aromatics, passes to the o-xylene tower from which o-xylene is taken off as overhead, and heavy ends are removed. The overhead from the xylene splitter column is transferred to conventional crystallization separation. The crystallizer operates in the manner described in Machell, et al., U.S. Pat. No. 3,662,013, dated May 9, 1972, the entire contents of which are incorporated herein by reference.

Because its melting point is much higher than that of the other $C_8$ aromatics, para-xylene (p-xylene) is readily separated in the crystallizer after refrigeration of the stream, and a xylene mixture lean in p-xylene is transferred to an isomerization unit. The isomerization charge passes through a heater, is admixed with hydrogen, and the mixture is introduced to the isomerizer.

Isomerized product from the isomerizer is cooled and passed to a high pressure separator from which separated hydrogen can be recycled in the process. The liquid product of the isomerization passes to a stripper from which light ends are passed overhead. The remaining liquid product comprising primarily $C_{8+}$ hydrocarbons is recycled in the system to the inlet of the xylene splitter.

It will be seen that the system is adapted to produce quantities of p-xylene from a mixed $C_8$ aromatic feed containing all of the xylene isomers plus ethylbenzene. The key to efficient operation to accomplish that result is the use of the isomerizer which takes crystallizer effluent lean in p-xylene and converts the other xylene isomers in part to p-xylene for further recovery at the crystallizer.

Among the xylene isomerization processes available in the art, Octafining was originally unique in its ability to convert ethylbenzene. Other xylene isomerization processes have required extremely expensive fractionation to separate ethylbenzene from other $C_8$ aromatic fractions. As set forth in the table of properties above, the boiling point of ethylbenzene is very close to those of p and m-xylene. Complete removal of ethylbenzene from the charge by conventional methods, e.g., distillation, is therefore impractical. The usual expedient for solving the problem involved the use of an ethylbenzene separation column in the isomerizer-separator loop when using catalyst other than those used in Octafining. However, Octafining does not require the use of this expensive auxiliary equipment to prevent build up of ethylbenzene in the loop. This advantageous feature is possible because the Octafining catalyst converts ethylbenzene to xylenes.

In Octafining, ethylbenzene reacts through ethyl cyclohexane to dimethyl cyclohexanes, which in turn equilibrate to xylenes. Competing reactions are disproportionation of ethylbenzene to ethane and benzene, and hydrocracking of alkyl cyclohexanes.

A significant improvement of the Octafining process arose with the introduction of zeolite catalysts, such as zeolite ZSM-5, combined with a metal, such as platinum, as described by Morrison, in U.S. Pat. No. 3,856,872. At temperatures of about 700°-800° F., ethylbenzene is converted by disproportionation over ZSM-5 type catalyst to benzene and diethylbenzene. At higher temperatures, and in the presence of a ZSM-5 catalyst of reduced activity, ethylbenzene and other single ring aromatics are converted by splitting off side chains of two or more carbon atoms as described in U.S. Pat. No. 4,188,282.

These developments permit upgrading of Octafining reactors by the substitution of the improved (ZSM-5) catalyst.

In the known processes for accepting ethylbenzene to the loop, conversion of that compound is constrained by the need to hold conversion of xylenes to other compounds to an acceptable level. Thus, although the Morrison technique provides significant advantages over Octafining in this respect, operating conditions are still selected to balance the advantages of ethylbenzene conversion against the disadvantages of xylene loss by disproportionation and the like.

A further advance in the art is described in patents to Morrison and Tabak, directed to various techniques for reducing acid activity of ZSM-5 zeolite catalyst, and use of such low activity catalysts for xylene isomerization concurrently with ethylbenzene conversion at temperatures upwards of 800° F. For example, U.S. Pat. No. 4,163,028, the entire contents of which are incorporated herein by reference, discloses xylene isomerization and ethylbenzene conversion at high temperature with the ZSM-5 zeolite of very high silica/alumina ratio, whereby the acid activity of the catalyst is reduced.

The inventions of those patents are predicated on discovery of combinations of catalyst and operating conditions which decouple ethylbenzene conversion from xylene loss in a xylene isomerization reaction, thus permitting the use of $C_8$ fractions, which contain ethylbenzene as the feed without sacrifice of xylenes to conditions which will promote adequate conversion of ethylbenzene. These results are obtained by the use of a catalyst characterized by zeolite ZSM-5 substantially reduced in activity, e.g., by dilution, steaming, very high silica/alumina ratio, base exchange with alkali metal, coking or the like. At the high temperatures of 800°-1000° F., the zeolite of reduced activity exhibits effective power for isomerization of xylene and for splitting off alkyl side chains of two or more carbon atoms from single ring aromatics at long on-stream periods. The disproportionation activity of the zeolite is severely depressed by the reduced acid activity, resulting in low losses of xylene by that mechanism. That lack of disproportionation activity impairs the capacity of the catalyst to handle trialkyl aromatics of nine or more carbon atoms, e.g., trimethylbenzene, as practiced in some processes. It thus becomes necessary to remove from the recycle stream those components having more than eight carbon atoms to avoid excessive build-up in the system of $C_9$ and higher hydrocarbons. The catalyst also has the capacity to crack paraffins in the change to lower boiling compounds readily removable from recycle streams by fractionators normally present in the p-xylene recovery/isomerizer loop.

By reason of this combination of activities, the catalyst may be used in a system charging reformate without removal of paraffin hydrocarbons, as described in U.S. Pat. No. 4,211,836.

The catalysts of zeolite, plus a metal, such as platinum discussed above, are of the type known as "dual function catalysts" characterized by the provision of catalyst sites of different functions, each of which separately performs its function, often one step for each type of site in a multi-step reaction sequence. Such catalysts and the sequential reaction steps catalyzed by different sites are discussed and explained by P. B. Weisz, "Polyfunctional Heterogeneous Catalysis," Advances in Catalysis, 13, pp 137-190 (1962). Weisz describes some experiments in which the two types of sites are provided by separate entities, such as physical mixtures of particles each of which provides only one type of catalytic site. Isomerization of certain paraffins over physical mixtures of acidic silica-alumina and platinum on a carrier is specifically described.

SUMMARY OF THE INVENTION

It has now been found that aromatic feedstocks containing $C_8$ aromatics can be effectively isomerized to produce a higher proportion of para-xylene (p-xylene) than contained in the feedstock in the presence of ZSM-22 zeolite. The isomerization process may optionally be conducted in the presence of hydrogen, and the catalyst may optionally contain a noble metal component, e.g., platinum.

DETAILED DESCRIPTION OF THE INVENTION

The isomerization process of this invention may also selectively dealkylate single ring aromatic compounds to remove alkyl side chains of two or more carbon atoms. The ZSM-22 zeolite catalyst has a silica/alumina mole ratio of at least 20 and a Constraint Index of about 2.6 at 800° F., as described in detail in a copending U.S. patent application of E. W. Valyocsik, Ser. No. 373,452, filed Apr. 30, 1982, and summarized below. The ZSM-22 zeolite catalyst may be optionally combined with a hydrogenation metal from Groups VIB or VIII of the Periodic Table, e.g., cobalt, nickel, tungsten, rhodium, molybdenum, platinum, palladium or combinations thereof. Preferably, the metal is platinum or palladium. The hydrogenation metal is present in the amount of about 0.005% by weight to about 5.0% by weight, based on total catalyst weight. The reactor is maintained at a temperature of about 500° to about 1100° F., preferably about 600° to about 1000° F., and a pressure of about 0 to about 3000 pounds per square inch gauge (psig), preferably about 50 to about 800 psig.

In general, it is desirable to operate the process of this invention in the presence of hydrogen gas to extend catalyst life and maintain good efficiency. The hydrogen to hydrocarbon mole ratio may be from about 0.1 to about 10, and preferably from about 0.5 to about 5.0, with a total pressure from about 0 up to about 3000 psig. The space velocity is usually adjusted to provide a desired conversion of ethylbenzene per cycle, usually from about 10 to 40%, and with the para isomer content of at least about 70%, preferably at least about 90% that of equilibrium.

The reactor of this invention may be incorporated in a reaction train through which a petroleum naphtha is processed for manufacture of p-xylene. Alternatively, the process of the invention may be used in a facility utilizing a feedstock of purchased $C_8$ aromatics or mixed xylenes. Typically a light petroleum naphtha is supplied to a catalytic reformer operated to convert naphthenes to aromatics by dehydrogenation under hydrogen pressure over a catalyst of platinum supported on alumina.

In one embodiment, aromatic rich reformate product of the reformer is fractionated to separate compounds of about eight carbon atoms ($C_8$) which is then extracted with a suitable selective solvent to separate aromatics from paraffins and provide a $C_8$ aromatics fraction. The $C_8$ aromatics fraction prepared by the solvent extraction stage may be fractionated for removal of some ethylbenzene. The degree of ethylbenzene removal, if practiced, may be accommodated to the desires of the operator, since the reactor of this invention can tolerate considerable amounts of ethylbenzene, which is converted to benzene. The $C_8$ aromatic fraction, optionally containing varying amounts of ethylbenzene, is conducted to the high temperature isomerizer of the present invention, wherein the isomerization of xylenes to yield increased p-xylene content product takes place.

However, the ZSM-22 zeolite catalyst used in this invention also has the capability to convert paraffins to lower boiling alkanes and alkenes which are readily separable by fractionation, and the invention contemplates charging of an unextracted $C_8$ fraction of the reformer product. Thus, if desired, the full range reformate may be charged to the isomerizer containing ZSM-22 zeolite in order to make benzene, toluene and xylenes (BTX) from higher boiling aromatics in the manner and under the conditions described in U.S. Pat. No. 4,188,282, the entire contents of which are incorporated herein by reference.

In any event, fresh feed to the isomerizer contains the $C_8$ aromatic fraction, optionally containing paraffins, and containing some ethylbenzene. The feed also usually contains the xylenes generated by reforming, along with other aromatics boiling in the xylene range or higher.

Under the high temperature conditions prevailing in the reactor, the ZSM-22 catalyst has the capacity (1) to isomerize xylenes, thereby restoring equilibrium concentrations in the mixed xylenes of the feed to generate additional p-xylene, (2) to remove alkyl chains of two or more carbon atoms from single ring aromatics, leaving methyl groups to thereby generate BTX, and (3) to crack normal paraffins to lower boiling compounds which can be removed in the downstream fractionators.

The effluent of the reactor contains the three xylenes in proportions approaching the thermodynamic equilibrium value together with conversion products from reaction of ethylbenzene and higher boiling alkyl aromatics, as well as a portion of unreacted ethylbenzene and higher aromatics. The by-products of the reaction include benzene, toluene and xylenes derived by reactions of such compounds as ethylbenzene, methylethylbenzene and dimethylethylbenzene. The reaction mixture is fractionated to take compounds of five or less carbon atoms overhead, to withdraw benzene and toluene as a side stream, and the bottoms stream comprising substantially aromatics of eight or more carbon atoms. The bottoms fraction is then fractionated in a separate fractionator to remove therefrom aromatics of nine or more carbon atoms as bottoms. The overhead fraction of that fractionator, comprising eight carbon atom aromatics is transferred as feed to a p-xylene separator of a conventional design from which a fraction depleted in p-xylene is recycled to the isomerization reactor.

The reactor of this invention contains a crystalline alumino-silicate (zeolite) ZSM-22 catalyst. That catalyst promotes a reaction course which is unique at temperatures of 500° to 1100° F. Ethylbenzene in the charge is selectively cracked to benzene at little or no conversion of xylenes. Two or more carbon atom chains on other aromatics undergo similar conversion. The two types of conversion are decoupled such that reaction severity is not a compromise to achieve effective ethyl aromatic conversion at "acceptable" loss of xylene. This characteristic of the process renders unnecessary the preliminary distillation to separate at least some of the ethylbenzene and $C_9$ + aromatics from the feed stream, as practiced in prior art processes.

The ZSM-22 highly siliceous zeolite used in the process of this invention can be suitably prepared from a reaction mixture containing a source of silica, an alkane diamine, an alkali metal oxide or an alkaline earth metal oxide, e.g., sodium, potassium, cesium, calcium or strontium, water, and alumina, and having a composition, in terms of mole ratios of oxides, falling within the following ratios:

| Reactants | Broad | Preferred |
| --- | --- | --- |
| $SiO_2/Al_2O_3$ | 20 to ∞ | 30 to 1000 |
| $H_2O/SiO_2$ | 10 to 100 | 20 to 60 |
| $OH^-/SiO_2$ | 0 to 0.3 | 0.1 to 0.2 |
| $M^+/SiO_2$ | 0 to 2.0 | 0.1 to 1.0 |
| $RN/SiO_2$ | 0.01 to 2.0 | 0.05 to 1.0 | wherein RN is a functional group of $C_2$-$C_{12}$ alkane diamine of the type $H_2N-(CH_2)_n-NH_2$ (abbreviated $C_nDN$), n=2 to 12, and preferably is 5 to 8, and M is an alkali metal or an alkaline earth metal and maintaining the mixture at crystallization temperature until crystals of the ZSM-22 zeolite are formed. Thereafter, the crystals are separated from the liquid by any conventional means, washed and recovered. The ZSM-22 zeolite can be used in aromatics alkylation reactions (e.g., toluene alkylation by methanol and ethylene), toluene disproportionation, selective cracking of a meta/para-cymene mixture, and conversion of various oxygenates to gasoline-grade hydrocarbons.

Crystallization can be carried out at either static or stirred conditions in a reactor vessel, e.g., a polypropylene jar or teflon lined or stainless steel autoclaves at 80° C. (176° F.) to about 210° C. (410° F.) for about 6 hours to 150 days. Thereafter, the crystals are separated from the liquid and recovered. The composition can be prepared utilizing materials which supply the appropriate oxide. Such materials include aluminates, alumina, silicates, sodium silicate, silica hydrosol, silica gel, silicic acid, sodium, potassium or cesium hydroxide, and an alkane diamine. Suitable diamines are, e.g., ethanediamine, propanediamine, butanediamine, pentanediamine, hexanediamine, heptanediamine, octanediamine, nonanediamine, decanediamine, undecanediamine, duodecanediamine. The reaction mixture can be prepared either batchwise or continuously. Crystal size and crystallization time of the new crystalline material will vary with the nature of the reaction mixture employed and the crystallization conditions.

As set forth above, the ZSM-22 zeolite can be prepared at a relatively wide range of $SiO_2/Al_2O_3$ ratios of about 20 to about infinity (∞). However, it has been found that larger alkali metal cations, e.g., $K^+$ and $Cs^+$, are preferably used at the $SiO_2/Al_2O_3$ ratios of about 20 to about 90 to obtain ZSM-22 crystals substantially free of impurities or other zeolites. The potassium (K+) cation is preferred at such low $SiO_2/Al_2O_3$ ratios because cesium (Cs) appears to decrease the reaction rate. At the $SiO_2/Al_2O_3$ ratios of 90 or above, smaller cations, e.g., sodium (NA+) cations, are preferably used to produce substantially 100% crystalline ZSM-22.

The highly siliceous ZSM-22 zeolite comprises crystalline, three-dimensional continuous framework silicon-containing structures or crystals which result when all the oxygen atoms in the tetrahedra are mutually shared between tetrahedral atoms of silicon or aluminum, and which can exist with a network of mostly $SiO_2$, i.e., exclusive of any intracrystalline cations. Similar crystals form building blocks of materials, such as quartz, cristobalite and a long list of zeolite structures, such as ZSM-5, ZSM-11, ZSM-12, ZSM-23, ZSM-35, ZSM-38, ZSM-48 (described in European Patent Application Number 80,300,463 published Sep. 3, 1980 as Publication Number 0,015,132, the entire content of which is incorporated herein by reference), mordenite and perhaps even faujasite. Not all zeolite structures are known to exist at this time in predominantly $SiO_2$-containing compositions-so the above class of materials does not presently include some zeolites, such as zeolite A.

The ZSM-22 zeolite also may contain a relatively minor amount of $Al_2O_3$ and therefore can produce a product with a $SiO_2$ to $Al_2O_3$ ratio of about 20 to about infinity ($\infty$). In the as-synthesized form, the ZSM-22 zeolite has a calculated composition, in terms of moles of oxides, after dehydration, per 100 moles of silica, as follows:

(0.02 to 10)RN:(0 to 2)$M_{2/n}$O:(0to 5)$Al_2O_3$:100$SiO_2$ wherein RN is a functional group of $C_2$-$C_{12}$ alkane diamine and M is an alkali metal or an alkaline earth metal having a valence n, e.g., Na, K, Cs, Li, Ca or Sr.

ZSM-22 can further be identified by its sorptive characteristics and its X-ray diffraction pattern. The original cations of the as-synthesized ZSM-22 may be replaced at least in part by other ions using conventional ion exchange techniques. It may be necessary to precalcine the ZSM-22 zeolite crystals prior to ion exchange. The replacing ions introduced to replace the original alkali, alkaline earth and/or organic cations may be any that are desired so long as they can pass through the channels within the zeolite crystals. Desired replacing ions are those of hydrogen, rare earth metals, metals of Groups IB, IIA, IIB, IIIA, IIIB, IVA, IVB, VIB and VIII of the Periodic Table. Among the metals, those particularly preferred are rare earth metals, manganese, zinc and those of Group VIII of the Periodic Table.

The ZSM-22 zeolite has a definite X-ray diffraction pattern, set forth below in Table I, which distinguishes it from other crystalline materials.

TABLE I

| Most Significant Lines of ZSM-22 | |
|---|---|
| Interplanar d-spacings (Å) | Relative Intensity (I/Io) |
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |

TABLE I-continued

| Most Significant Lines of ZSM-22 | |
|---|---|
| Interplanar d-spacings (Å) | Relative Intensity (I/Io) |
| 2.52 ± 0.02 | W |

These values were determined by standard techniques. The radiation was the K-alpha doublet of copper and a diffractometer equipped with a scintillation counter and an associated computer was used. The peak heights, I, and the positions as a function of 2× theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in A, corresponding to the recorded lines, were determined. In Table I, the relative intensities are given in terms of the symbols vs=very strong, s=strong, m=medium, w=weak, etc. It should be understood that this X-ray diffraction pattern is characteristic of all the species of ZSM-22 zeolite composition. Ion exchange of the alkali metal cations with other ions results in a zeolite which reveals substantially the same X-ray diffraction pattern with some minor shifts in interplanar spacing and variation in relative intensity. Other minor variations can occur, depending on the silica to alumina ratio of the particular sample, as well as its degree of thermal treatment.

The ZSM-22 zeolite freely sorbs normal hexane and has a pore dimension greater than about 4 Angstroms. In addition, the structure of the zeolite must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous hydrocarbon conversions, although puckered structures exist, such as TMA offretite, which is a known effective zeolite. Also, such twelve-membered structures can be conceived that may be operative due to pore blockage or other causes.

Rather than attempt to judge from crystal structure whether or not a zeolite possesses the necessary constrained access, a simple determination of the "Constraint Index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. (288° C.) and 950° F. (510° C.) to give an overall conversion between 10% and 60%. The mixture of hydrocarbons is passed at a 1 liquid hourly space velocity (LHSV), i.e., 1 volume of liquid hydrocarbon per volume of zeolite per hour over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons.

Constraint Index (CI) values for some typical zeolites are:

| Zeolite | Constraint Index |
| --- | --- |
| ZSM-5 | 8.3 |
| ZSM-11 | 8.7 |
| ZSM-12 | 2 |
| ZSM-23 | 9.1 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina (non-zeolite) | 0.6 |
| Erionite | 38 |

It is to be realized that the above Constraint Index values typically characterize the specified zeolites but that these are the cumulative result of several variables used in determination and calculation thereof. Thus, for a given zeolite, depending on the temperature employed within the aforenoted range of 550° F. to 950° F., with accompanying conversion between 10% and 60%, the Constraint Index may vary within the indicated approximate range of 1 to 12. Likewise, other variables, such as the crystal size of the zeolite, the presence of possible occluded contaminants and binders intimately combined with the zeolite, may affect the Constraint Index. It will accordingly be understood by those skilled in the art that the Constraint Index, as utilized herein, while affording a highly useful means for characterizing the zeolites of interest is an approximate value, taking into consideration the manner of its determination; with probability, in some instances, of compound variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratio. In those instances, a temperature of up to about 1000° F. and a liquid hourly space velocity of less than one, such as 0.1 or less, can be employed in order to achieve a minimum total conversion of about 10%.

Synthetic ZSM-22 zeolites can be used in the process of this invention either in the organic nitrogen-containing and alkali metal-containing form, the alkali metal form and hydrogen form or another univalent or multivalent cationic form. The as-synthesized zeolite may be conveniently converted into the hydrogen, the univalent or multivalent cationic forms by base exchanging the zeolite to remove the sodium cations by such ions as hydrogen (from acids), ammonium, alkylammonium and arylammonium including $RNH_3$, $R_3NH^+$, $R_2NH_2^+$ and $R_4N^+$ where R is alkyl or aryl, provided that steric hindrance does not prevent the cations from entering the cage and cavity structure of the ZSM-22 type crystalline zeolite. The hydrogen form of the zeolite is prepared, for example, by base exchanging the sodium form with a suitable ammonium ion, e.g., ammonium chloride or hydroxide, whereby the ammonium ion is substituted for the sodium ion. The composition is then calcined at a temperature of, e.g., 1000° F. (about 540° C.), causing evolution of ammonia and retention of the hydrogen proton in the composition. Other replacing cations include cations of the metals of the Periodic Table, particularly metals other than sodium, most preferably metals of Group IIA, e.g., zinc, and Groups IIIA, IVA, IB, IIB, IIIB, IVB, VIB and Group VIII of the Periodic Table, and rare earth metals and manganese.

Ion exchange of the zeolite can be accomplished conventionally, e.g., by admixing the zeolite with a solution of a cation to be introduced into the zeolite. Ion exchange with various metallic and non-metallic cations can be carried out according to the procedures described in U.S. Pat. Nos. 3,140,251, 3,140,252 and 3,140,253, the entire contents of which are incorporated herein by reference.

The ZSM-22 zeolite can optionally be used in this invention in intimate combination with a hydrogenating component, such as tungsten, vanadium, molybdenum, rhenium, nickel, cobalt, chromium, manganese, or a noble metal, such as platinum or palladium where a hydrogenation-dehydrogenation function is desired. Such component can be exchanged into the composition, impregnated therein or physically intimately admixed therewith. Such component can be impregnated in or onto the zeolite, for example, in the case of platinum, by treating the zeolite with a solution containing a platinum metal-containing ion. Thus, suitable platinum compounds include chloro-platinic acid, platinous chloride and various compounds containing the platinum tetrammine-platinum complex. Combinations of the aforementioned metals and methods for their introduction can also be used.

Synthetic ZSM-22 zeolite, when employed as a catalyst in this process, should be at least partially dehydrated. This can be accomplished by heating the zeolite to a temperature in the range of about 200° C. to about 600° C. in an inert atmosphere, such as air or nitrogen for about 1 to about 48 hours. Simple dehydration of the crystal can also be performed at lower temperatures, such as room temperature, merely by placing the ZSM-22 zeolite type crystal in a vacuum, but a longer time is required to obtain a sufficient degree of dehydration.

It may also be desired to incorporate the ZSM-22 crystal with another material resistant to the temperatures and other conditions employed in organic conversion processes. Such materials include active and inactive materials and synthetic or naturally occurring zeolites as well as inorganic materials, such as clays, silica and/or metal oxides. The clays, silica and/or metal oxides may be either naturally occurring or in the form of gelatinous precipitates or gels including mixtures of silica and metal oxides. The use of such additional active materials in conjunction with the ZSM-22 crystal, i.e., combined therewith, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Such materials, e.g., clays or oxides, function as binders for the catalyst. It is desirable to provide a catalyst having good crush strength because in commercial use it is desirable to prevent the catalyst from breaking down into powder-like materials. These clay binders are normally employed for the purpose of improving the crush strength of the catalyst.

Naturally occurring clays which can be composited with the ZSM-22 zeolite include the montmorillonite and kaolin family, which families include the subbentonites, and the kaolins commonly known as Dixie, McNamee-Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the ZSM-22 crystal also include inorganic oxides, e.g., alumina.

In addition to the foregoing materials, the ZSM-22 zeolite can be composited with a porous matrix material, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The relative proportions of finely divided crystalline material and inorganic oxide gel matrix vary widely, with the crystal content ranging from about 1 to about 90% by weight.

The invention utilizes the ZSM-22 zeolites of the type described above, preferably those forms of the ZSM-22 zeolites which are of relatively low acidity. As the acid activity of these zeolites is reduced, the capacity to catalyze disproportionation declines without substantial decline in the capacity to catalyze dealkylation of such compounds as ethylbenzene having side chains of two or more carbon atoms. Therefore, the isomerization reaction may be decoupled from the ethylbenzene conversion which now proceeds by dealkylation in the presence of the low acidity ZSM-22 zeolite. A significant consequence of this catalytic property is that recycle of toluene and trimethylbenzene to the reactor is generally undesirable because, due to the lack of disproportionation activity, methylbenzenes will not be converted in significant amounts to xylenes. Hence, recycle of these unreactive species would result in an undesirable build-up in the loop of diluent materials.

The low acid activity of the catalyst can be obtained in a variety of manners including forming the ZSM-22 zeolite at high silica/alumina ratio above 200, preferably above 500. Very high dilution with an inert matrix is also effective in lowering the acid activity of ZSM-22 zeolite. For example, composites of a more active form of zeolite ZSM-22 with alumina at a ratio of 5 parts of zeolite and 95 parts of the inert matrix provide a suitable low acid activity catalyst.

ZSM-22 zeolites employed in severe reactions, such as aromatization of paraffins and olefins, lose activity to an extent which makes them suitable for use in the process of this invention. See, e.g., U.S. Pat. No. 3,960,978, the entire contents of which are incorporated herein by reference, for fuller discussion of this manner of deactivating zeolite. Another method for reducing activity of ZSM-22 zeolites is to provide basic cations, such as sodium, at a significant proportion of the cationic sites of the zeolite. That technique, as applied to ZSM-5 zeolites, is described in U.S. Pat. No. 3,899,544, the entire contents of which are incorporated herein by reference.

Little differences in process chemistry is found with ZSM-22 catalyst of low activity achieved by techniques other than steaming, although it may exhibit higher aging rates as measured by the temperature increase required to maintain constant ethylbenzene conversion.

It is considered preferable for purposes of this invention to steam the ZSM-22 catalyst prior to its use in the process of this invention to control its acid activity. In particular, the unsteamed catalyst, which may be referred to herein as the precursor catalyst, is steamed under relatively mild conditions, such as for about one to about ten hours with 100% steam at atmospheric pressure and at a temperature of about 800° F. to 1000° F. to reduce its acidity to a measured "Alpha" value in the range of 5 to 50. It is to be understood, of course, that the treating conditions may be altered from those recited, such as by using superatmospheric pressure at reduced temperature, the critical parameter being the controlled acidity of the steamed catalyst.

The controlled acid activity of the catalyst is conveniently defined by the "Alpha" scale described in an article published in Journal of Catalysis, Vol. VI, pp. 278–287 (1966), which publication is incorporated herein by reference. In the alpha test, the catalyst is contacted with hexane under prescribed conditions, and the amount of hexane which is cracked is measured. From this measurement is computed the "Alpha" value used herein. For purposes of the present invention, however, all measurements of "Alpha" are to be made at 1000° F., and all references to "Alpha" are to be understood to refer to the value obtained when the hexane cracking is measured at 1000° F.

Any combination of the aforementioned methods may be used to lower the acid activity of the ZSM-22 zeolite.

In order to more fully illustrate the nature of the invention and the manner of practicing same, the following examples are presented.

In the examples which follow, and elsewhere in the specification, whenever adsorption data are set forth for comparison of sorptive capacities for water, cyclohexane and n-hexane, they were determined as follows:

A weighed sample of the calcined zeolite was contacted with the desired pure adsorbate vapor in an adsorption chamber, evacuated to <1 mm pressure and contacted with water vapor at 12 mm Hg or n-hexane or cyclohexane vapor at 20 mm Hg pressure, pressures less than the vapor-liquid equilibrium pressure of the respective adsorbate at room temperature. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the pressures to the aforementioned control levels. Sorption was complete when the pressure change was not sufficient to activate the manostat.

The increase in weight was calculated as the adsorption capacity of the sample in g/100 g of calcined adsorbent.

EXAMPLE A

Catalyst Preparation

Solution A, containing 192.0 g. of silica sol (30% $SiO_2$) and 200.0 g. water, was mixed with stirring with Solution B, containing 6.7 g. $Al_2(SO_4)_3.16H_2O$, 15.5 g. KOH, 33.4 g. 1,6-hexanediamine ($C_6DN$), and 351.2 g. water, directly into a one-liter stainless steel autoclave. The composition of reaction mixture, in mole ratios, was: $SiO_2/Al_2O_3=90$; $H_2O/SiO_2=40$; $OH^-/SiO_2=0.20$; $K^+/SiO_2=0.29$; $C_6DN/SiO_2=0.30$.

The thus formed hydrogel was heated at 160° C. with stirring (400 rpm) for 2 days at autogenous pressure. The resultant crystalline product was filtered, washed with water, and dried on a filter funnel at 110° C. X-ray and scanning electron microscopy (SEM) analysis of the product crystals revealed 100% crystalline ZSM-22 with needle-like crystal morphology (0.5–1.0 m in length). The crystals had $SiO_2/Al_2O_3$ mole ratio of 76 as determined by chemical analysis.

A portion of the sample of the zeolite was heated in a tube furnace in flowing nitrogen (150 ml/ml) at a rate of 2° C./min to 550° C., whereupon the flowing gas was switched to air. The sample was heated in air at 550° C. for 24 hours, then cooled to room temperature.

The calcined zeolite was now placed in a canister and ballmilled for 17 hours. This ballmilling procedure was capable of fracturing the needle-like ZSM-22 crystals to smaller, roughly equidimensional crystals, without loss of x-ray crystallinity.

The ballmilled crystals were now $NH_4^+$—exchanged in one molar (1M) $NH_4NO_3$ solution twice at 80° C., with stirring, for a total of 6 hours, filtered, washed with water, then dried.

The material was then mixed with alumina monohydrate in a 65% zeolite, 35% alumina preparation and extruded to produce 1/16 inch cylindrical particles.

EXAMPLE B

Catalyst Preparation

Solution A, containing 192.0 g. silica sol (30% $SiO_2$) and 200.0 g. water, was mixed with stirring with Solution B, containing 3.4 g. $Al_2(SO_4)_3.16H_2O$, 5.5 g. NaOH, 33.4 g. 1,6-hexanediamine ($C_6DN$), and 354.1 g. water, directly into a one-liter stainless steel autoclave. The composition of this mixture, in mole ratios, was: $SiO_2/Al_2O_3=180$; $H_2O/SiO_2=40$; $OH^-/SiO_2=0.10$; $Na^+/SiO_2=0.14$; $C_6DN/SiO_2=0.30$.

The hydrogel was heated at 160° C., with stirring at 400 rpm, at autogenous pressure for 3 days. The crystalline product was filtered, washed with water, and dried. X-ray and SEM analysis of the product showed 100% crystalline ZSM-22 crystals with needle-like morphology (1.0 μm in length). The $SiO_2/Al_2O_3$ mole ratio of the product was 156.

5.2 g. of this product was heated for 10 hours in flowing dry $N_2$ gas. When cooled to 25° C., it was saturated with $NH_3$ gas, followed by ion exchanges for 4, 16 and 4 hours, respectively, with 260 ml. of 2N $NH_4NO_3$. It was then washed at reflux with 260 ml. of water, followed by an air calcination for 10 hours at 600° C. Finally, 0.75 g. of this material, sized to 14–30 mesh, was impregnated with 2 ml. of aqueous solution containing 0.011% of $Pt(NH_3)_4Cl_2$. This final product contained 0.013% Pt on HZSM-22.

EXAMPLE 1

Isomerization Process

A synthetic $C_8$ aromatic feed was passed over the catalyst of Example A at 200 psig, hydrogen:hydrocarbon mole ration ($H_2/HC$) of 4, and temperatures and weight hourly space velocity (WHSV) of between 850° and 900° F., and 5 and 20, respectively. The experimental conditions, and feed and product analyses are given in Table 2. As can be seen, at 900° F. and WHSV=5, near equilibrium p-xylene concentrations are achieved (93% of equilibrium) and xylene selectivity is very good (xylene loss is less than 1.3%).

EXAMPLE 2

Isomerization Process

A synthetic $C_8$ aromatic feed was passed over the catalyst of Example B at temperatures between 900° and 1052° F. and WHSV between 5 and 20 and at 200 psig and $H_2/HC=4$. The experimental conditions and feed and product analyses are summarized in Table 3. At 900° F. and WHSV=5 (Samples 1, 4 and 10), high isomerization activity is demonstrated by near equilibrium (92% of equilibrium) concentrations of p-xylene and the xylene selectivity is very good (xylene losses are less than 0.35%).

TABLE 2

| Sample | Feed | 1 | 2 | 3 | 4 | 5 | 6 | 7 |
|---|---|---|---|---|---|---|---|---|
| Time On Stream | | | | | | | | |
| (hrs) | | 16.23 | 28.13 | 29.63 | 32.97 | 34.63 | 36.14 | 39.49 |
| (days) | | 0.68 | 1.17 | 1.23 | 1.37 | 1.44 | 1.51 | 1.64 |
| Temperature (°F.) | | 901 | 899 | 899 | 850 | 851 | 861 | 902 |
| Pressure (psig) | | 200 | 200 | 200 | 200 | 200 | 200 | 200 |
| $H_2$/HC (psig) | | 4 | 4 | 4 | 4 | 4 | 4 | 4 |
| WHSV | | 5 | 10 | 20 | 5 | 10 | 20 | 5 |
| Liquid Product Analyses (Wt. %) | | | | | | | | |
| Light gas | | 1.33 | 0.55 | 0.31 | 0.00 | 0.26 | 0.17 | 0.95 |
| Benzene | | 3.16 | 1.59 | 0.86 | 1.64 | 0.85 | 0.45 | 2.86 |
| Toluene | 0.10 | 1.00 | 0.43 | 0.25 | 0.48 | 0.28 | 0.19 | 0.80 |
| n-$C_9$ | | | | | | | | - |
| ethylbenzene (EB) | 19.73 | 14.63 | 16.99 | 17.36 | 16.76 | 17.90 | 18.58 | 15.09 |
| p-xylene[a] | 9.46 | 18.26 | 16.80 | 14.28 | 17.93 | 15.64 | 13.36 | 17.99 |
| | 11.8 | 23.2 | 21.1 | 17.6 | 22.33 | 19.49 | 16.63 | 22.71 |
| m-xylene[a] | 50.57 | 41.72 | 44.89 | 47.05 | 43.93 | 46.17 | 48.19 | 42.49 |
| | 63.1 | 53.1 | 56.3 | 58.2 | 54.71 | 57.53 | 59.98 | 53.64 |
| o-xylene[a] | 20.10 | 18.64 | 18.09 | 19.58 | 18.43 | 18.44 | 18.80 | 18.73 |
| | 25.1 | 23.7 | 22.7 | 24.2 | 22.95 | 22.98 | 23.40 | 23.65 |
| Ethyl toluene (ETol) | | 0.26 | 0.11 | 0.04 | 0.03 | 0.03 | 0.03 | 0.10 |

TABLE 2-continued

| Sample | Feed | 1 | 2 | 3 | 4 | 5 | 6 | 7 |
|---|---|---|---|---|---|---|---|---|
| Trimethyl benzene (TMB) | | 0.28 | 0.12 | 0.05 | 0.19 | 0.08 | 0.01 | 0.24 |
| para-diethyl benzene (p-DEB) | 0.40 | 0.25 | 0.14 | 0.37 | 0.20 | 0.10 | 0.40 | |
| m,o-DEB | | 0.03 | 0.01 | 0.01 | 0.02 | 0.01 | 0.00 | 0.03 |
| dimethyl ethyl benzene (DMEB) | 0.31 | 0.12 | 0.03 | 0.04 | 0.04 | 0.01 | 0.27 | |
| Other | | | | | | | | |
| $C_9^+$ (total) | | 1.28 | 0.61 | 0.27 | 0.65 | 0.36 | 0.15 | 1.04 |
| Total xylenes | 80.13 | 78.62 | 79.78 | 80.90 | 80.29 | 80.25 | 80.35 | 79.21 |
| p-xylene (% of Equilibrium) | 49.2 | 96.8 | 87.7 | 73.5 | 93.0 | 81.20 | 69.3 | 94.6 |
| Benzene/EB Conv. | | 0.83 | 0.77 | 0.48 | 0.74 | 0.62 | 0.52 | 0.82 |
| EB/EB (%) | | 25.8 | 13.9 | 12.0 | 15.05 | 9.28 | 5.83 | 23.5 |
| Xyl/Xyl (%) | | 1.22 | 0.51 | 0.19 | 0.40 | 0.20 | 0.05 | 0.73 |
| Ratio | | 21.2 | 27.4 | 63.1 | 37.6 | 46.4 | 116. | 32.2 |

[a]Numbers appearing immediately below this line are percentages of the indicated xylenes in the total xylene product.

TABLE 3

| Sample | Feed | 1 | 2 | 3 | 4 | 5 | 6 | 7 | 8 | 9 | 10 |
|---|---|---|---|---|---|---|---|---|---|---|---|
| Time On Stream | | | | | | | | | | | |
| (hrs) | | 4.21 | 6.58 | 8.12 | 21.49 | 25.88 | 29.87 | 31.41 | 33.03 | 35.11 | 51.24 |
| (days) | | 0.18 | 0.27 | 0.34 | 0.90 | 1.08 | 1.24 | 1.31 | 1.38 | 1.46 | 2.14 |
| Temperature (°F.) | | 900 | 901 | 902 | 900 | 904 | 900 | 950 | 1000 | 1052 | 902 |
| Pressure (psig) | | 200 | 200 | 200 | 200 | 200 | 200 | 200 | 200 | 200 | 200 |
| $H_2$/HC (psig) | | 4 | 4 | 4 | 4 | 4 | 4 | 4 | 4 | 4 | 4 |
| WHSV | | 5 | 10 | 20 | 5 | 7.5 | 20 | 20 | 20 | 20 | |
| Liquid Product Analyses (Wt. %) | | | | | | | | | | | |
| Light gas | | 3.65 | 1.27 | 0.60 | 4.56 | 1.67 | 0.77 | 0.93 | 1.35 | 1.80 | 1.99 |
| Benzene | | 4.17 | 2.16 | 1.22 | 5.30 | 2.93 | 1.26 | 2.07 | 3.28 | 4.67 | 4.13 |
| Toluene | 0.10 | 1.34 | 0.67 | 0.35 | 1.37 | 0.75 | 0.29 | 0.65 | 0.98 | 1.76 | 0.94 |
| n-$C_9$ | | | | | | | | | | | |
| ethylbenzene (EB) | 19.73 | 12.50 | 15.93 | 17.29 | 12.51 | 14.86 | 17.42 | 16.42 | 14.66 | 12.53 | 13.69 |
| p-xylene[a] | 9.46 | 17.21 | 16.46 | 14.37 | 17.04 | 16.86 | 14.01 | 15.02 | 16.04 | 16.43 | 17.44 |
| | 11.8 | 22.2 | 20.7 | 17.9 | 22.6 | 21.30 | 17.5 | 18.9 | 20.2 | 20.9 | 22.2 |
| m-xylene[a] | 50.57 | 43.77 | 42.50 | 48.04 | 42.51 | 45.53 | 47.10 | 46.59 | 45.18 | 44.01 | 44.17 |
| | 63.1 | 56.5 | 56.9 | 59.9 | 56.3 | 57.5 | 58.9 | 58.5 | 57.0 | 56.0 | 56.2 |
| o-xylene[a] | 20.10 | 16.48 | 17.74 | 17.81 | 15.95 | 16.78 | 18.84 | 18.02 | 18.05 | 18.15 | 17.03 |
| | 25.1 | 21.3 | 22.3 | 22.2 | 21.1 | 21.2 | 23.6 | 22.6 | 22.8 | 23.1 | 21.7 |
| Ethyl toluene (ETol) | | 0.22 | 0.15 | 0.06 | 0.16 | 0.16 | 0.05 | 0.08 | 0.13 | 0.18 | 0.17 |
| Trimethyl benzene (TMB) | | 0.04 | 0.01 | 0.05 | 0.03 | 0.02 | 0.02 | 0.07 | 0.06 | 0.08 | 0.02 |
| para-diethyl benzene (p-DEB) | | 0.21 | 0.15 | 0.11 | 0.18 | 0.13 | 0.04 | 0.07 | 0.11 | 0.17 | 0.16 |
| m,o-DEB | | 0.19 | 0.03 | 0.00 | 0.14 | 0.15 | 0.14 | 0.18 | 0.09 | 0.08 | 0.16 |
| dimethyl ethyl benzene (DMEB) | | 0.04 | 0.02 | 0.00 | 0.00 | 0.05 | 0.01 | 0.03 | 0.03 | 0.05 | 0.02 |
| Other | | | | | | | | | | | |
| $C_9^+$ (total) | | 0.70 | 0.36 | 0.22 | 0.51 | 0.51 | 0.26 | 0.33 | 0.42 | 0.56 | 0.53 |
| Total xylenes | | 77.46 | 79.40 | 80.22 | 75.50 | 79.17 | 79.95 | 79.63 | 79.27 | 78.59 | 78.64 |
| p-xylene (% of Equilibrium) | | 92.6 | 86.4 | 74.6 | 94.0 | 88.7 | 73.0 | 78.6 | 84.3 | 87.1 | 92.4 |
| Benzene/EB Conv. | | 0.77 | 0.76 | 0.66 | 0.84 | 0.80 | 0.73 | 0.83 | 0.86 | 0.86 | 0.91 |
| EB/EB (%) | | 36.6 | 19.3 | 12.42 | 36.6 | 24.70 | 11.71 | 16.78 | 25.70 | 36.49 | 30.61 |
| Xyl/Xyl (%) | | 0.30 | 0.17 | 0.14 | 0.20 | 0.22 | 0.09 | 0.22 | 0.25 | 0.34 | 0.20 |
| Ratio | | 122.0 | 113.5 | 87.3 | 187.2 | 112.3 | 130.1 | 76.3 | 102.8 | 107.3 | 153.0 |

[a]Numbers appearing immediately below this line are percentages of the indicated xylenes in the total xylene product.

It will be apparent to those skilled in the art that the specific embodiments discussed above can be successfully repeated with ingredients equivalent to those generically or specifically set forth above and under variable process conditions.

From the foregoing specification one skilled in the art can readily ascertain the essential features of this invention and without departing from the spirit and scope thereof can adapt it to various diverse applications.

We claim:

1. In a process for isomerizing xylenes from a hydrocarbon mixture to produce a product stream comprising substantially an equilibrium mixture of xylene isomers, said process comprising contacting the hydrocarbon mixture with a catalyst comprising a zeolite, the improvement for selectively isomerizing said xylenes by minimizing xylene loss due to undesired side reactions, said improvement comprising selecting as said zeolite a ZSM-22 zeolite having a silica:alumina mole ratio of at least about 20 and having the X-ray diffraction pattern of Table I.

2. A process of claim 1 wherein such amount of hydrogen is admixed with the hydrocarbon mixture that the hydrogen to hydrocarbon mole ratio is about 0.1 to about 10.

3. A process of claim 2 wherein the hydrogen to hydrocarbon mole ratio is about 0.5 to about 5.0.

4. A process of claim 3 wherein the acid activity of the as-synthesized ZSM-22 zeolite has been reduced.

5. A process of claim 4 wherein the acid activity of the ZSM-22 zeolite is 5 to 50 on the Alpha scale.

6. A process of claim 5 wherein the acid activity of the as-synthesized ZSM-22 zeolite has been reduced by steaming.

7. A process of claim 6 wherein the catalyst comprises a Group VIB or Group VIII metal.

8. A process of claim 7 wherein the metal is a noble metal of Group VIII of the Periodic Table of Elements.

9. A process of claim 8 wherein the metal is platinum or palladium.

10. A process of claims 8 or 9 wherein the amount of metal in the catalyst is about 0.005% by weight to about 5.0% by weight, based on total catalyst weight.

11. A process of claim 10 wherein the isomerization is conducted at the temperature of about 500° F. to about 1100° F. and at a pressure of about 0 to about 3000 psig.

12. A process of claim 11 wherein the isomerization is conducted at the temperature of about 600° F. to about 1000° F. and a pressure of about 50 to about 800 psig.

13. A process of claim 12 wherein the product stream comprises at least about 70% of the equilibrium amount of para-xylene.

14. A process of claim 13 wherein the product stream comprises at least about 90% of the equilibrium amount of para-xylene.

15. A process of claim 14 wherein the acid activity of the as-synthesized ZSM-22 zeolite has been reduced by steaming it for about 1 to about 10 hours with 100% steam at atmospheric pressure at a temperature of about 800° F. to 1000° F.

* * * * *